US011557038B2

(12) United States Patent
Chae et al.

(10) Patent No.: US 11,557,038 B2
(45) Date of Patent: Jan. 17, 2023

(54) APPARATUS AND METHOD FOR X-RAY DATA GENERATION

(71) Applicant: ELECTRONICS AND TELECOMMUNICATIONS RESEARCH INSTITUTE, Daejeon (KR)

(72) Inventors: Seung-Hoon Chae, Daejeon (KR); Sooyeul Lee, Daejeon (KR); Jeongwon Lee, Daejeon (KR); Seunghwan Kim, Daejeon (KR); Yoon Seon Song, Daejeon (KR); Ji Wook Jeong, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 231 days.

(21) Appl. No.: 17/072,496

(22) Filed: Oct. 16, 2020

(65) Prior Publication Data

US 2021/0118131 A1 Apr. 22, 2021

(30) Foreign Application Priority Data

Oct. 17, 2019 (KR) .................. 10-2019-0128840
Sep. 28, 2020 (KR) .................. 10-2020-0125381

(51) Int. Cl.
*G06T 7/00* (2017.01)
*G06T 5/20* (2006.01)
(Continued)

(52) U.S. Cl.
CPC .......... *G06T 7/0012* (2013.01); *A61B 6/5205* (2013.01); *A61B 6/5294* (2013.01);
(Continued)

(58) Field of Classification Search
CPC .......... G06T 7/0012; G06T 3/40; G06T 5/20; G06T 2207/10116; G06T 2207/20084; G06V 20/647; A61B 6/5205; A61B 6/594
See application file for complete search history.

(56) References Cited

U.S. PATENT DOCUMENTS 10,186,038 B1 * 1/2019 Kluckner .............. G06V 10/82
10,346,977 B2 7/2019 Chae et al.
(Continued)

FOREIGN PATENT DOCUMENTS

JP      2018082767 A     5/2018
KR   1020180099039 A     9/2018
WO   WO-2005059592 A1 *  6/2005    .......... G06T 11/005

*Primary Examiner* — Shefali D Goradia

(57) ABSTRACT

The apparatus for an X-ray data generation according to an embodiment of the inventive concept includes a processor that receives 3D data to generate output data and a buffer, and the processor includes an extraction unit that extracts raw object data from the 3D data and projects the raw object data onto a 2D plane to generate first object data, an augmentation unit that performs data augmentation on the first object data to generate second object data, a composition unit that synthesizes the second object data and background data to generate composite data, and a post-processing unit that performs post-processing on the composite data to generate the output data, and the buffer stores a plurality of parameters related to generation of the first object data, the second object data, the composite data, and the output data.

16 Claims, 11 Drawing Sheets

(51) Int. Cl.
    *A61B 6/00* (2006.01)
    *G06T 3/40* (2006.01)
    *G06V 20/64* (2022.01)

(52) U.S. Cl.
    CPC ................ *G06T 3/40* (2013.01); *G06T 5/20* (2013.01); *G06V 20/647* (2022.01); *G06T 2207/10116* (2013.01); *G06T 2207/20084* (2013.01)

(56) References Cited

U.S. PATENT DOCUMENTS

| | | | |
|---|---|---|---|
| 10,846,552 B1* | 11/2020 | Wu | G06V 10/255 |
| 10,939,044 B1* | 3/2021 | Tagra | H04N 5/232933 |
| 2016/0211045 A1* | 7/2016 | Jeon | A61B 6/487 |
| 2018/0196158 A1 | 7/2018 | Fu et al. | |
| 2018/0197320 A1 | 7/2018 | Lim et al. | |
| 2018/0286087 A1 | 10/2018 | Ray et al. | |
| 2019/0034976 A1* | 1/2019 | Hamedi | G06Q 30/0243 |
| 2019/0362522 A1 | 11/2019 | Han | |
| 2020/0211187 A1* | 7/2020 | Zhang | G16H 50/50 |
| 2020/0342635 A1* | 10/2020 | Rajvanshi | G06T 11/60 |
| 2021/0027470 A1* | 1/2021 | Lin | G06N 3/082 |
| 2021/0064872 A1* | 3/2021 | Kim | G06N 3/04 |
| 2021/0073953 A1* | 3/2021 | Lee | G06T 7/571 |
| 2022/0028129 A1* | 1/2022 | Balashova | G06N 20/00 |

\* cited by examiner

APPARATUS AND METHOD FOR X-RAY DATA GENERATION

CROSS-REFERENCE TO RELATED APPLICATIONS

This application claims priority under 35 U.S.C. § 119 to Korean Patent Application Nos. 10-2019-0128840 filed on Oct. 17, 2019, and 10-2020-0125381 filed on Sep. 28, 2020, respectively, in the Korean Intellectual Property Office, the disclosures of which are incorporated by reference herein in their entireties.

BACKGROUND

Embodiments of the inventive concept described herein relate to an X-ray data generation, and more particularly, relate to an apparatus and a method for an X-ray data generation, which are used for neural network learning.

Artificial intelligence is being used in various fields due to the development of its technology. Since a predictive performance of neural networks used in artificial intelligence is determined depending on a learning method of a neural network, it is necessary to learn the neural network using high-quality learning data. However, when the neural network is learned using only data acquired in an actual environment, the amount of learning data is limited, and it is difficult to secure learning data that reflects various environments. In addition, to learn the neural network using data acquired in the actual environment, additional processing for the acquired data is required, and additional annotation work for learning may be required in the acquired data.

Furthermore, in the case of an X-ray image, the number of samples is less than that of a general visible ray image, and it is limited to acquire images in various environments due to the characteristics of photographing devices. Therefore, in the medical field or the customs detection field where X-ray images are mainly used, it is difficult to secure learning data for introducing artificial intelligence.

SUMMARY

Embodiments of the inventive concept provide an apparatus and a method for generating X-ray data used for learning of a neural network that performs an X-ray image analysis.

According to an embodiment of the inventive concept, an apparatus for an X-ray data generation includes a processor that receives 3D data to generate output data and a buffer, and the processor includes an extraction unit that extracts raw object data from the 3D data and projects the raw object data onto a 2D plane to generate first object data, an augmentation unit that performs data augmentation on the first object data to generate second object data, a composition unit that synthesizes the second object data and background data to generate composite data, and a post-processing unit that performs post-processing on the composite data to generate the output data, and the buffer stores a plurality of parameters related to generation of the first object data, the second object data, the composite data, and the output data.

According to an embodiment of the inventive concept, a method for an X-ray data generation includes extracting raw object data from 3D data and generating first object data by projecting the raw object data onto a 2D plane, generating second object data by performing data augmentation on the first object data, generating composite data by composing the second object data with background data, and generating output data by performing post-processing on the composite data.

BRIEF DESCRIPTION OF THE FIGURES

The above and other objects and features of the inventive concept will become apparent by describing in detail exemplary embodiments thereof with reference to the accompanying drawings.

DETAILED DESCRIPTION

Figure 1:
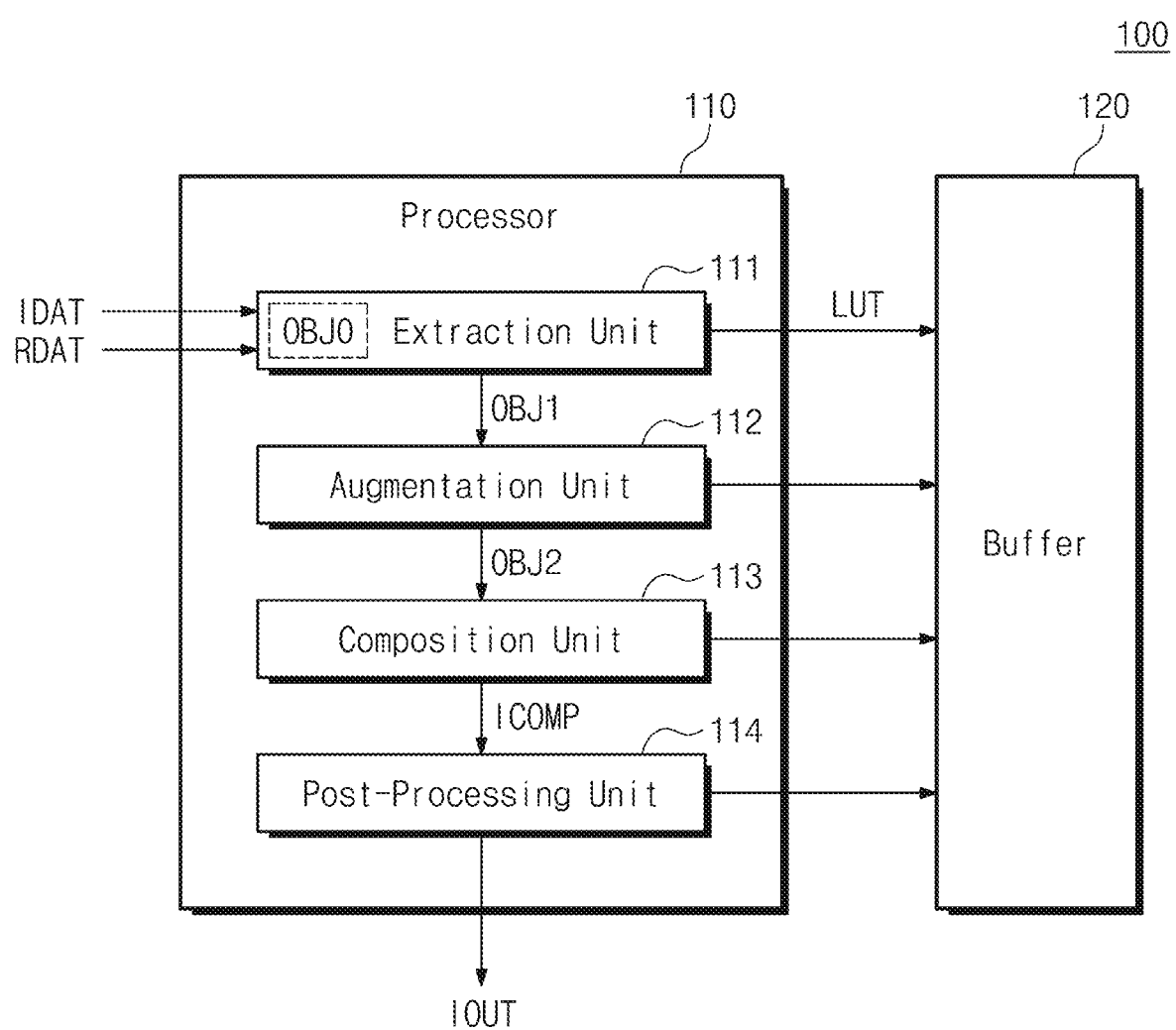
FIG. 1 is a block diagram illustrating an exemplary configuration of an apparatus for X-ray data generation according to an embodiment of the inventive concept.

Hereinafter, embodiments of the inventive concept will be described clearly and in detail such that those skilled in the art may easily carry out the inventive concept.

Components described with reference to terms such as parts or units, modules, blocks, and ~er or ~or, which are used in the detailed description and functional blocks illustrated in the drawings may be implemented in the form of software, hardware, or a combination of hardware and software. Illustratively, the software may be machine code, firmware, embedded code, or application software. For example, the hardware may include electrical circuits, electronic circuits, processors, computers, integrated circuits, integrated circuit cores, pressure sensors, inertial sensors, microelectromechanical systems (MEMS), passive elements, or combinations thereof.

FIG. 1 is a block diagram illustrating an exemplary configuration of an apparatus 100 for X-ray data generation according to an embodiment of the inventive concept. The apparatus 100 may include a processor 110 and a buffer 120.

The processor 110 may include an extraction unit 111, an augmentation unit 112, a composition unit 113, and a post-processing unit 114. The processor 110 may receive input data IDAT. For example, the input data IDAT may be 3D CT data obtained by photographing a real object (e.g., a cancer cell or a knife) using a computed tomography (CT) technique. The processor 110 may generate 2D object data, based on the received input data IDAT.

The processor 110 may generate X-ray data by composing the generated 2D object data with background data, and may generate output data IOUT that may be used for neural network learning by post-processing the generated X-ray data. For example, the processor 110 may include at least one of processing units such as a central processing unit (CPU), a graphics processing unit (GPU), a neural network processing unit (NPU), and an accelerated processing unit (APU).

The extraction unit 111 may extract raw object data OBJ0 (e.g., the cancer cell or the knife) which are targets to be analyzed from the input data IDAT. In the following descriptions, the raw object data OBJ0 will be referred to as an object OBJ0. For example, the extraction unit 111 may extract the object OBJ0 which are targets to be analyzed by applying edge detection algorithm or image segmentation algorithm with respect to the input data IDAT.

Figure 2:
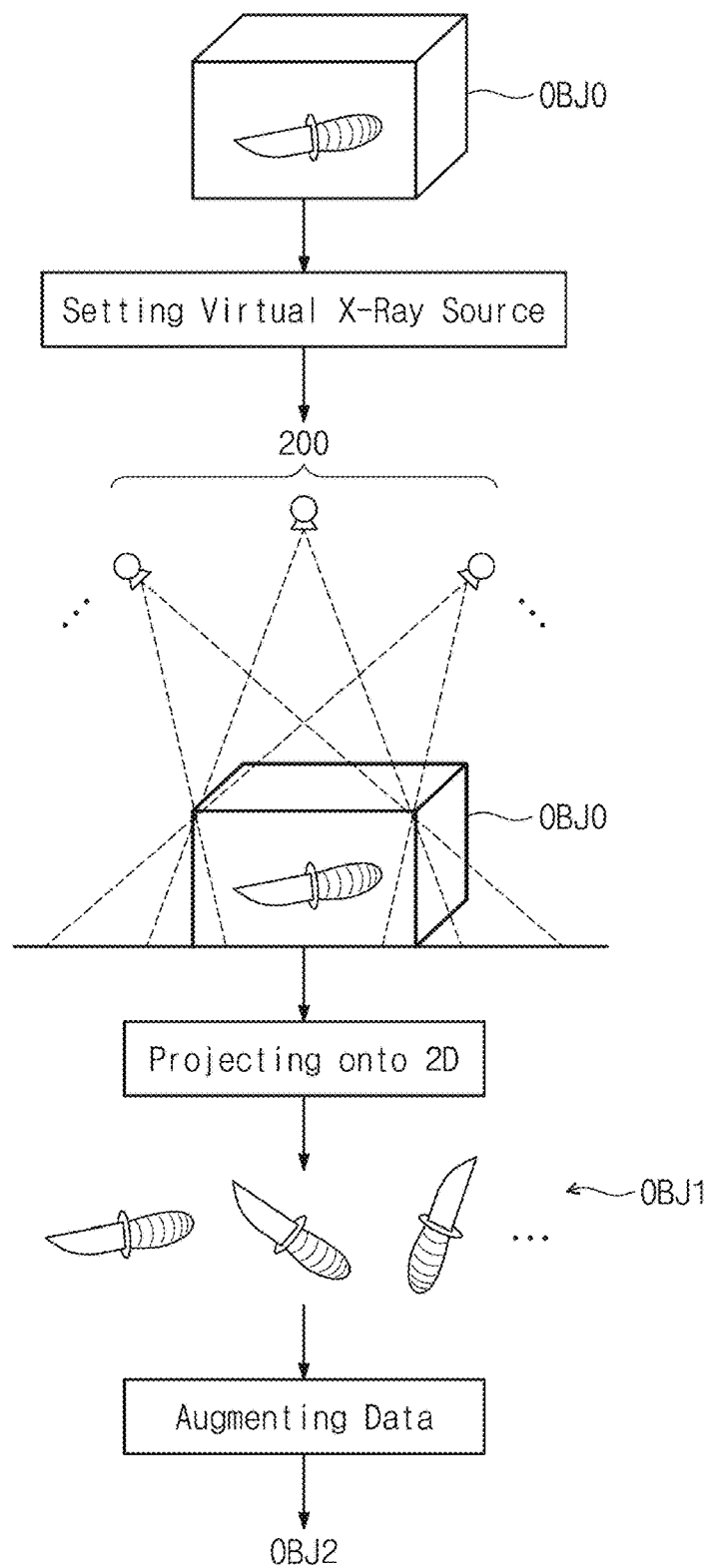
FIG. 2 is a diagram conceptually illustrating a process of generating first object data and second object data.

The extraction unit 111 may project the object OBJ0 extracted from the input data IDAT onto a 2D plane. The extraction unit 111 may set a virtual X-ray source at an arbitrary position to project the object OBJ0 extracted from the input data IDAT onto the 2D plane. For example, the virtual X-ray source may be set to be located outside the extracted object. The extraction unit 111 may generate an X-ray image obtained by irradiating a virtual X-ray toward the object extracted from the input data IDAT through the set virtual X-ray source as first object data OBJ1. Referring to FIG. 2, a process of generating the first object data OBJ1 is illustrated.

The extraction unit 111 may generate the first object data OBJ1 in which the object OBJ0 extracted from the input data IDAT is projected onto the 2D plane at various angles by using the virtual X-ray source as described above. For example, even when the object OBJ0 is extracted from the input data IDAT photographed in a horizontal direction, the extraction unit 111 may generate the first object data OBJ1 in a vertical direction. As in the above description, even when the object OBJ0 is extracted from the input data IDAT photographed in the vertical direction, the extraction unit 111 may generate the first object data OBJ1 in the horizontal direction. Accordingly, the extraction unit 111 may simultaneously generate the first object data OBJ1 in the horizontal direction and the vertical direction. The extraction unit 111 photographs the same subject as the input data IDAT at the same angle, but may additionally receive reference data RDAT set differently only for the photographing energy (e.g., the X-ray energy used for CT photographing). The extraction unit 111 may generate a lookup table LUT indicating a correspondence relationship between the photographing X-ray energy and an attenuation coefficient of the object OBJ0, based on the input data IDAT and the reference data RDAT. The extraction unit 111 may store the generated lookup table LUT in the buffer 120. A process of generating the lookup table LUT by the extraction unit 111 will be described with reference to FIGS. 10 to 11.

In another embodiment, when it is difficult to extract the object from the input data IDAT, the extraction unit 111 may generate the first object data OBJ1 by projecting the entire input data IDAT onto the 2D plane using the virtual X-ray source and then by extracting the object which are targets to be analyzed from a 2D X-ray image.

The extraction unit 111 may store a plurality of parameters (e.g., a location of the extracted object, a size of the extracted object, location information of the virtual X-ray source, etc.) that are related to extracting the object from the input data IDAT and projecting onto the 2D plane in the buffer 120.

The augmentation unit 112 may generate second object data OBJ2 by performing a data augmentation with respect to the first object data OBJ1 generated by the extraction unit 111. For example, the data augmentation may include a moving of data, a rotating of data, or a resizing of data. The data augmentation of the first object data OBJ1 may be limited depending on properties of the object which are targets to be analyzed. For example, when the object which are targets to be analyzed is the cancer cell, a size of the cancer cell may vary depending on a stage of cancer progression, and thus a size change of the first object data OBJ1 may be limited.

The augmentation unit 112 may perform a data rotation to generate the second object data OBJ2 having various angles from the first object data OBJ1. For example, the augmentation unit 112 may generate the second object data OBJ2 in the vertical direction by performing the data rotation on the first object data OBJ1 in the horizontal direction. Likewise, the augmentation unit 112 may generate the second object data OBJ2 in the horizontal direction by performing the data rotation on the first object data OBJ1 in the vertical direction. Accordingly, the augmentation unit 112 may simultaneously generate the second object data OBJ2 in the horizontal direction and the second object data OBJ2 in the vertical direction.

The augmentation unit 112 may store a plurality of parameters (e.g., coordinates of a position where data are moved, an angle at which data are rotated, a size before and after data change, etc.) that are related to the data augmentation of the first object data OBJ1 in the buffer 120.

The composition unit 113 may generate composite data ICOMP by composing the second object data OBJ2 generated by the augmentation unit 112 with background data. The composition unit 113 may store a plurality of background data, and may select the background data corresponding to the second object data OBJ2. The background data may vary depending on a type of object which are targets to be analyzed and a purpose of an analysis.

For example, when the type of the object which are targets to be analyzed is the cancer cell, and the purpose of the analysis is to generate data for learning a medical neural network, the composition unit 113 may select an image representing an organ of a human body as the background data. For example, when the type of the object which are targets to be analyzed is the knife, and the purpose of the analysis is to generate data for learning a neural network for customs detection, the composition unit 113 may select an image of a truck including a container box as the background data.

The composition unit 113 may determine a composition possible region indicating a region in which the second object data OBJ2 may be located on the background data, based on the type of the object which are targets to be analyzed and the purpose of the analysis. For example, when the object which are targets to be analyzed is a lung cancer cell and the purpose of the analysis is to generate data for learning the medical neural network, the composition unit 113 may determine a region in which the lungs are located in the human body as the composition possible region. For example, when the object which are targets to be analyzed is the knife and the purpose of the analysis is to generate data for learning the neural network for customs detection, the composition unit 113 may determine a region inside the container box excluding the truck as the composition possible region.

Figure 3:
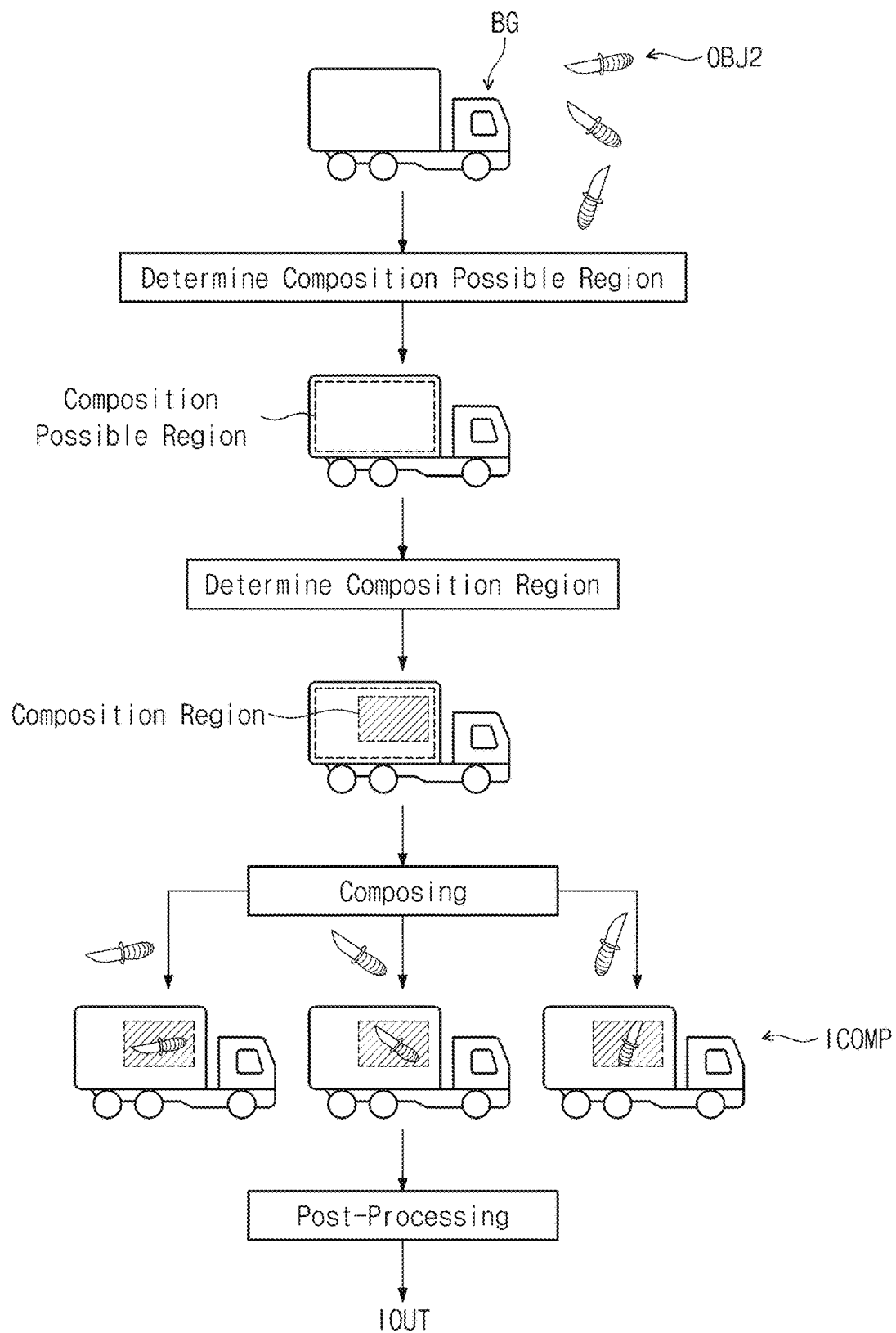
FIG. 3 is a diagram conceptually illustrating a process of generating composite data and output data.

The composition unit 113 may determine a composition region in which the second object data OBJ2 are actually composed from the determined composition possible region. Referring to FIG. 3, the composition possible region and the composition region on background data are illustrated as an example.

In another embodiment, the composition unit 113 may be implemented as software stored in a non-transitory computer-readable medium to receive the composition region from a user. In this case, the composition unit 113 may provide a user interface through which the composition region may be input on a display device (not illustrated). An embodiment in which the composition unit 113 is implemented as software will be described with reference to FIG. 9.

The composition unit 113 may generate the composite data ICOMP by composing the second object data OBJ2 with the determined composition region.

The composition of the second object data OBJ2 and the background data may be performed based on a feature of attenuation in intensity when the X-ray passes through the subject.

In general, the intensity I of the X-ray that passes through the subject in a straight line may be expressed as Equation 1 below.

$$I = I_0(v)\exp\left(-\int \mu(E, t)dt\right)$$ [Equation 1]

$I_0(v)$ is the intensity of X-ray at a location v of the X-ray detector (i.e., a location where there is no subject), which may represent the intensity of the X-ray for air where the subject is not located. $\mu(E,t)$ is the attenuation coefficient of the subject, may indicate a degree to which the intensity of the X-ray is attenuated depending on the length when passing through the subject of a specified thickness, and may be different by the energy E of the X-ray and the thickness t of the subject.

In addition, when there are two subjects, the intensity I of the X-ray passing through the first subject and the second subject in the straight line may be expressed as Equation 2 below.

$$I=I_0(v)\exp(-\int\mu_1(E,t)dt)\exp(-\int\mu_2(E,t)dt)$$ [Equation 2]

$\mu_1(E,t)$ represents the attenuation coefficient of the first subject, and $\mu_2(E,t)$ represents the attenuation coefficient of the second subject.

As illustrated through Equation 1 and Equation 2, using the feature that the intensity of the X-ray is attenuated depending on the attenuation coefficient of the subject located on the path of the X-ray, the location of the subject may be indicated on arbitrary background data. That is, the X-ray image may include a plurality of pixels, and each of the plurality of pixels may represent the attenuation coefficient of the subject located in each pixel.

Accordingly, the composition unit 113 may generate the composite data ICOMP by multiplying an attenuation coefficient value corresponding to each pixel of the background data by an attenuation coefficient value corresponding to each pixel of the second object data OBJ2. For example, the composition unit 113 may generate the composite data ICOMP in which the knife is composed on the container box by multiplying the value of the attenuation coefficient corresponding to each pixel of the container box by the value of the attenuation coefficient corresponding to each pixel of the knife. Referring to FIG. 3, the composite data ICOMP obtained by composing a plurality of knives on the container box are illustrated. The composition unit 113 may multiply the value of an attenuation coefficient corresponding to each pixel of the second object data OBJ2 by a generated arbitrary weight. When the weight is multiplied, the second object data OBJ2 may appear more clearly on the composite data ICOMP.

Figure 4:
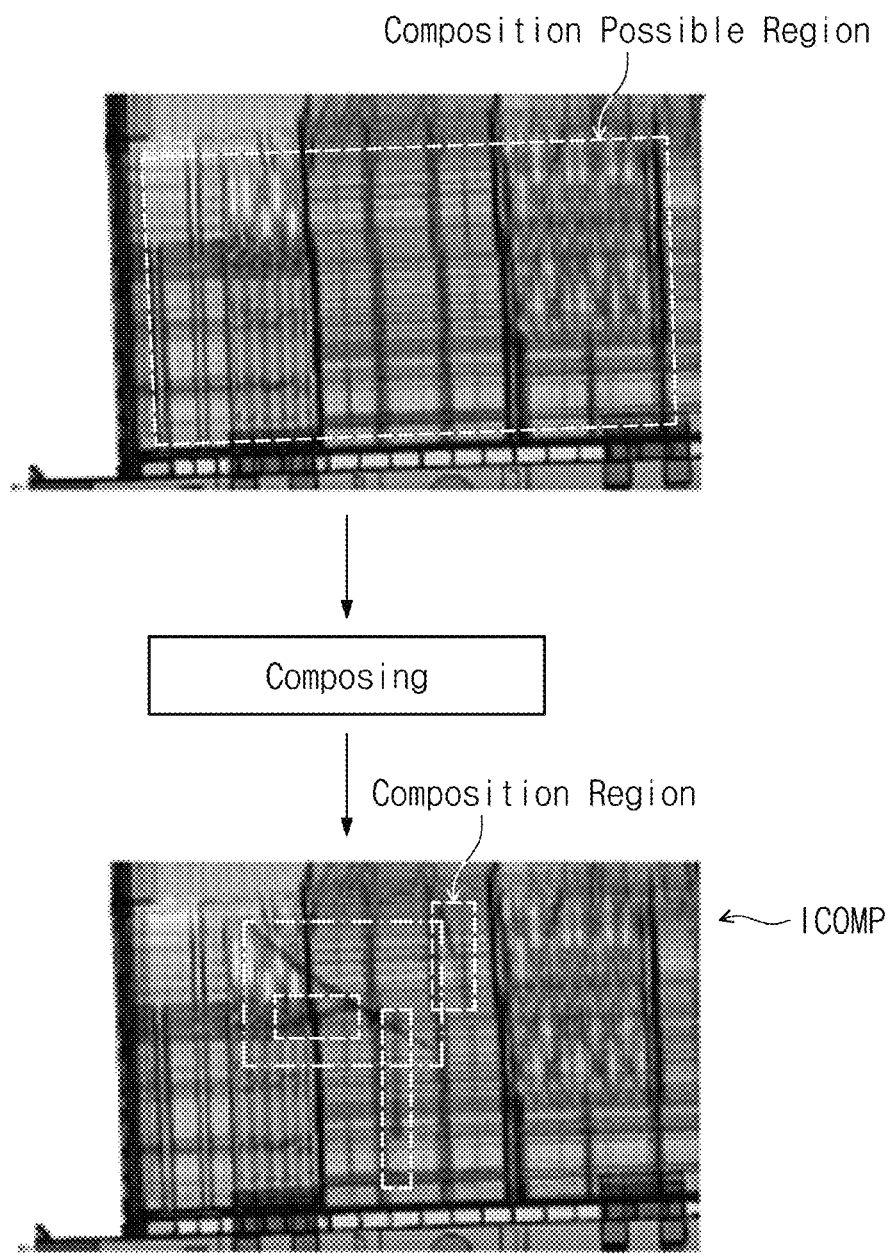
FIG. 4 is a diagram describing composite data in which a plurality of objects are composed with respect to one background data.

When there are a plurality of the object data, the composition unit 113 may generate the composite data ICOMP by multiplying the value of the attenuation coefficient corresponding to each pixel of the background data by the value of the attenuation coefficient corresponding to each pixel of each of the plurality of object data. For example, the composition unit 113 may generate composite data ICOMP in which the plurality of knives are composed on the container box by multiplying the value of the attenuation coefficient corresponding to each pixel of the container box by the value of the attenuation coefficient corresponding to each pixel of each of the plurality of knives. Referring to FIG. 4, the composite data ICOMP obtained by composing the plurality of knives on the container box are illustrated together with the composition region (as illustrated by a dotted line).

The composition unit 113 may perform a conversion of the photographing X-ray energy on the second object data OBJ2 before performing the composition of the background data and the second object data OBJ2. For example, when it is necessary to match the photographing X-ray energy of the background data and the photographing X-ray energy of the second object data OBJ2, the composition unit 113 may convert the photographing X-ray energy on the second object data OBJ2. Accordingly, the composition unit 113 may match the photographing X-ray energy of the second object data OBJ2 with the photographing X-ray energy of the background data.

As illustrated through Equation 1 and Equation 2, the attenuation coefficient of the subject may vary depending on the energy of the X-ray irradiated during photographing. Therefore, the conversion of the photographing X-ray energy of the subject may be performed by replacing the value (i.e., the value of the attenuation coefficient depending on the energy before conversion) of the attenuation coefficient corresponding to each pixel of the subject with the value of the attenuation coefficient depending on the energy to be converted.

To perform the above-described energy conversion, the composition unit 113 may invoke the lookup table LUT indicating a correspondence relationship between the X-ray energy and the attenuation coefficient of the subject from the buffer 120. For example, the lookup table LUT may indicate the correspondence relationship between the attenuation coefficients when the second object data OBJ2 is generated based on a first energy and the attenuation coefficient when the second object data OBJ2 is generated based on a second energy.

For example, in the case of converting the photographing X-ray energy of the second object data OBJ2 from the first energy to the second energy, the composition unit 113 may refer to the lookup table LUT and may replace the value (i.e., the value of the attenuation coefficient depending on the first energy) of the attenuation coefficient corresponding to each pixel of the second object data OBJ2 with the value of the attenuation coefficient depending on the second energy. Accordingly, the photographing X-ray energy of the second object data OBJ2 may be converted from the first energy to the second energy.

The composition unit 113 may store a plurality of parameters (e.g., a position of the composition possible region, a position of the composition region, the attenuation coefficient, etc.) that are related to the composition of the background data and the second object data OBJ2 in the buffer 120.

The post-processing unit 114 may perform post-processing on the composite data ICOMP generated by the composition unit 113 to generate output data IOUT in which a sense of heterogeneity between the background data and the object is resolved. For example, the post-processing unit 114 may generate the output data IOUT by blurring a boundary line between the background data and the object. However, the inventive concept is not limited thereto, and the composition unit 113 may not output the composite data ICOMP to the post-processing unit 114 but may directly output the composite data ICOMP as the output data IOUT.

The post-processing unit 114 may include a Generative Adversarial Network (GAN). For example, the post-processing unit 114 may generate output data IOUT in which the sense of heterogeneity between the background data and the object is resolved, based on the GAN.

The GAN may include a generative model and a classification model. The generative model may receive the composite data ICOMP and may generate a plurality of composite data in which the sense of heterogeneity is removed. The classification model may receive the plurality of composite data in which the sense of heterogeneity is removed and a plurality of non-composite data, and may learn to determine whether the received data are composed.

After the classification model sufficiently learns to determine whether data are composed, the classification model may relearn the generative model, based on a result of determining whether data are composed. For example, when the classification model erroneously determines that the composition is not performed with respect to the composite data in which the sense of heterogeneity is removed, the generative model may be learned to additionally generate the composite data in which the sense of heterogeneity is removed. The classification model may relearn to determine whether to compose or not, based on data additionally generated from the generative model.

Accordingly, the post-processing unit 114 may improve the performance of the generative model by repeatedly and competitively learning the generative model and the classification model based on the GAN, and may generate output data IOUT in which the sense of heterogeneity is eliminated from the composite data ICOMP by using only the generative model after the performance of the generative model is improved. A process of post-processing based on the GAN will be described in more detail with reference to FIG. 8.

The post-processing unit 114 may store a plurality of parameters (e.g., information on how much the boundary line between the background data and the object is blurred, information related to GAN, etc.) that are related to performing post-processing in the buffer 120.

The buffer 120 may include the lookup table LUT for converting the photographing X-ray energy. The buffer 120 may include a plurality of parameters related to the extraction of the object, the 2D projection, the data augmentation, the composition between the background data and the object, and post-processing of the composite data, which are performed by the processor 110. The buffer 120 may annotate the plurality of parameters as additional information with respect to the output data IOUT.

FIG. 2 conceptually illustrates a process of generating first object data OBJ1 and second object data OBJ2. It will be described below with reference to FIG. 1 together with FIG. 2.

The extraction unit 111 may set a virtual X-ray source 200 at an arbitrary position to project the object OBJ0 extracted from the input data IDAT into a 2D space. The set virtual X-ray source 200 may irradiate X-ray toward the extracted object OBJ0 to generate an X-ray image projected onto the 2D space as the first object data OBJ1. For example, when the object which are targets to be analyzed is the knife, the first object data OBJ1 may be the X-ray image of the knife.

For example, the number of first object data OBJ1 generated by the extraction unit 111 may be the same as the number of set virtual X-ray source 200. The augmentation unit 112 may generate the second object data OBJ2 by performing data augmentation (e.g., the moving of data, the rotating of data, or the changing the size of data) on the first object data OBJ1.

FIG. 3 conceptually illustrates a process of generating the composite data ICOMP and the output data IOUT. It will be described below with reference to FIG. 1 together with FIG. 3.

The composition unit 113 may select background data BG corresponding to the second object data OBJ2. For example, when the type of an object which are targets to be analyzed is the knife, and the purpose of the analysis is to generate data for learning the neural network for customs detection, the composition unit 113 may select an image of the truck including the container box as the background data BG.

After selecting the background data BG, the composition unit 113 may determine the composition possible region in which the second object data OBJ2 may be located. For example, when the background data BG are the image of the truck including the container box, the composition possible region in which the second object data OBJ2 may be located may be a region inside the container box excluding the truck.

The composition unit 113 may determine a composition region in which the second object data OBJ2 are actually composed from the determined composition possible region. For example, when composing the knife in a region inside the container box, the composition region may be determined as a region (e.g., a hatched part) in which another goods (e.g., a box) capable of hiding the knife exists among regions inside the container box. The composition unit 113 may generate the composite data ICOMP by composing the second object data OBJ2 on the determined composition region.

The composition unit 113 may output the composite data ICOMP to the post-processing unit 114, and the post-processing unit 114 may perform post-processing on the composite data ICOMP to generate the output data IOUT. However, the inventive concept is not limited thereto, the composition unit 113 may not output the composite data ICOMP to the post-processing unit 114 but may directly output the composite data ICOMP as the output data IOUT.

FIG. 3 shows a case in which the composition unit 113 synthesizes one object with respect to one background data BG. However, the inventive concept is not limited thereto, as illustrated in FIG. 4, the composition unit 113 may generate the composite data ICOMP obtained by composing a plurality of objects (as marked with dotted borders and hatched lines) with respect to one background data BG.

Figure 5:
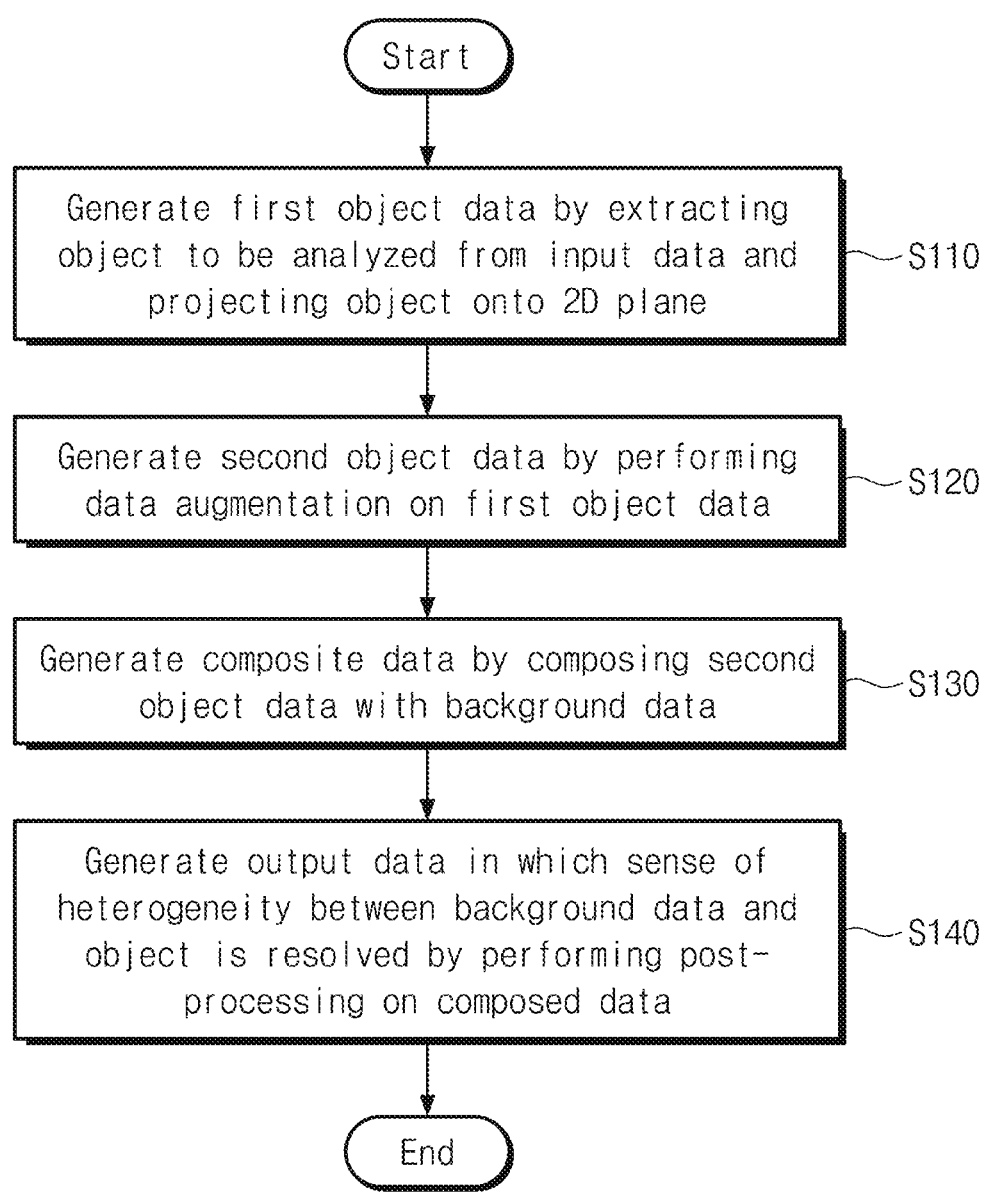
FIG. 5 is a flowchart describing a method for generating X-ray data according to an embodiment of the inventive concept.

FIG. 5 is a flowchart describing a method for generating X-ray data according to an embodiment of the inventive concept. It will be described below with reference to FIG. 1 together with FIG. 5.

In operation S110, the extraction unit 111 may generate the first object data OBJ1 by extracting the object OBJ0 which are targets to be analyzed from the input data IDAT and projecting the object OBJ0 onto the 2D plane. To project the object OBJ0 extracted from the input data IDAT onto the 2D plane, the extraction unit 111 may set the virtual X-ray source at an arbitrary position. The extraction unit 111 may generate the X-ray image obtained by irradiating the virtual X-ray toward the object OBJ0 extracted from the input data IDAT through the set virtual X-ray source as the first object data OBJ1.

In operation S120, the augmentation unit 112 may generate the second object data OBJ2 by performing the data augmentation on the first object data OBJ1. For example, the data augmentation may include a moving of the data, a rotating of the data, or a resizing of the data.

In operation S130, the composition unit 113 may generate the composite data ICOMP by composing the second object data OBJ2 with the background data. The composition of the second object data OBJ2 and the background data may be performed based on a feature of attenuation in intensity when X-ray passes through the subject.

In operation S140, the post-processing unit 114 may perform post-processing on the composite data ICOMP to generate the output data IOUT in which the sense of heterogeneity between the background data and the object is resolved.

Figure 6:
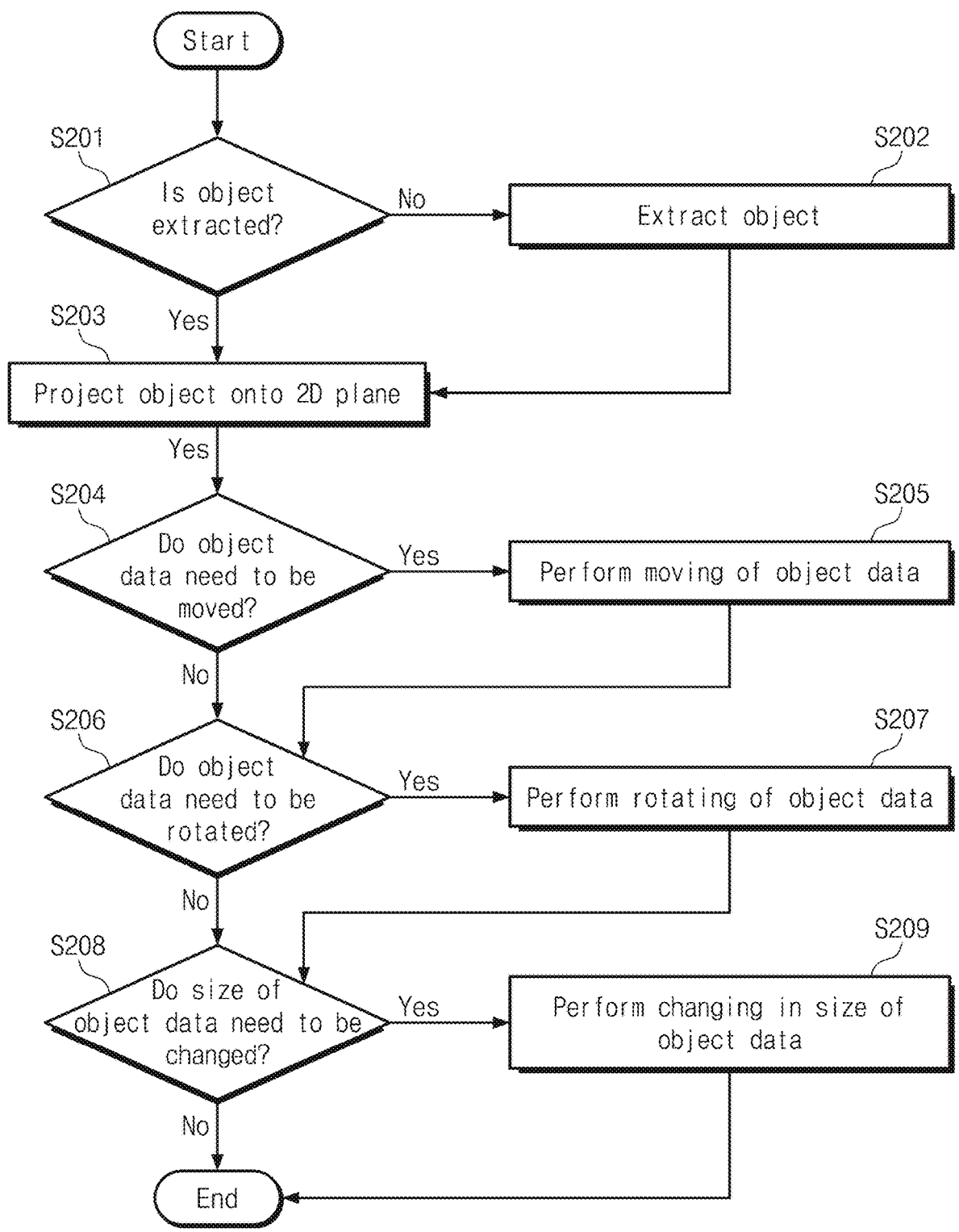
FIG. 6 is a flowchart describing an object extraction process and data augmentation process according to an embodiment of the inventive concept.

FIG. 6 is a flowchart describing an object extraction process and data augmentation process according to an embodiment of the inventive concept. It will be described below with reference to FIG. 1 together with FIG. 6.

In operation S201, the processor 110 may determine whether the extraction unit 111 extracts the object OBJ0 which are targets to be analyzed from the input data IDAT. When the object OBJ0 is not extracted, in operation S202, the extraction unit 111 may extract the object. When the object which are targets to be analyzed is extracted, in operation S203, the extraction unit 111 may project the extracted object OBJ0 onto the 2D plane, and may generate the first object data OBJ1. The following operations may be performed by the augmentation unit 112.

In operation S204, it may be determined whether the first object data OBJ1 need to be moved. When the first object data OBJ1 need to be moved, in operation S205, the first object data OBJ1 may be moved. In operation S206, it may be determined whether the first object data OBJ1 need to be rotated. When the first object data OBJ1 need to be rotated, in operation S207, the rotation of the first object data OBJ1 may be performed.

In operation S208, it may be determined whether the size of the first object data OBJ1 needs to be changed. When it is necessary to change the size of the first object data OBJ1, in operation S209, a size change of the first object data OBJ1 may be performed. The change in data size of the first object data OBJ1 may be limited depending on the property of the object which are targets to be analyzed. For example, when the object which are targets to be analyzed is the cancer cell, since the size of the cancer cell may vary depending on the stage of cancer progression, the size change of the first object data OBJ1 may be limited.

However, the inventive concept is not limited to the order illustrated in FIG. 6, and the object extraction and data augmentation on the first object data OBJ1 may be performed differently from the order illustrated in FIG. 6.

Figure 7:
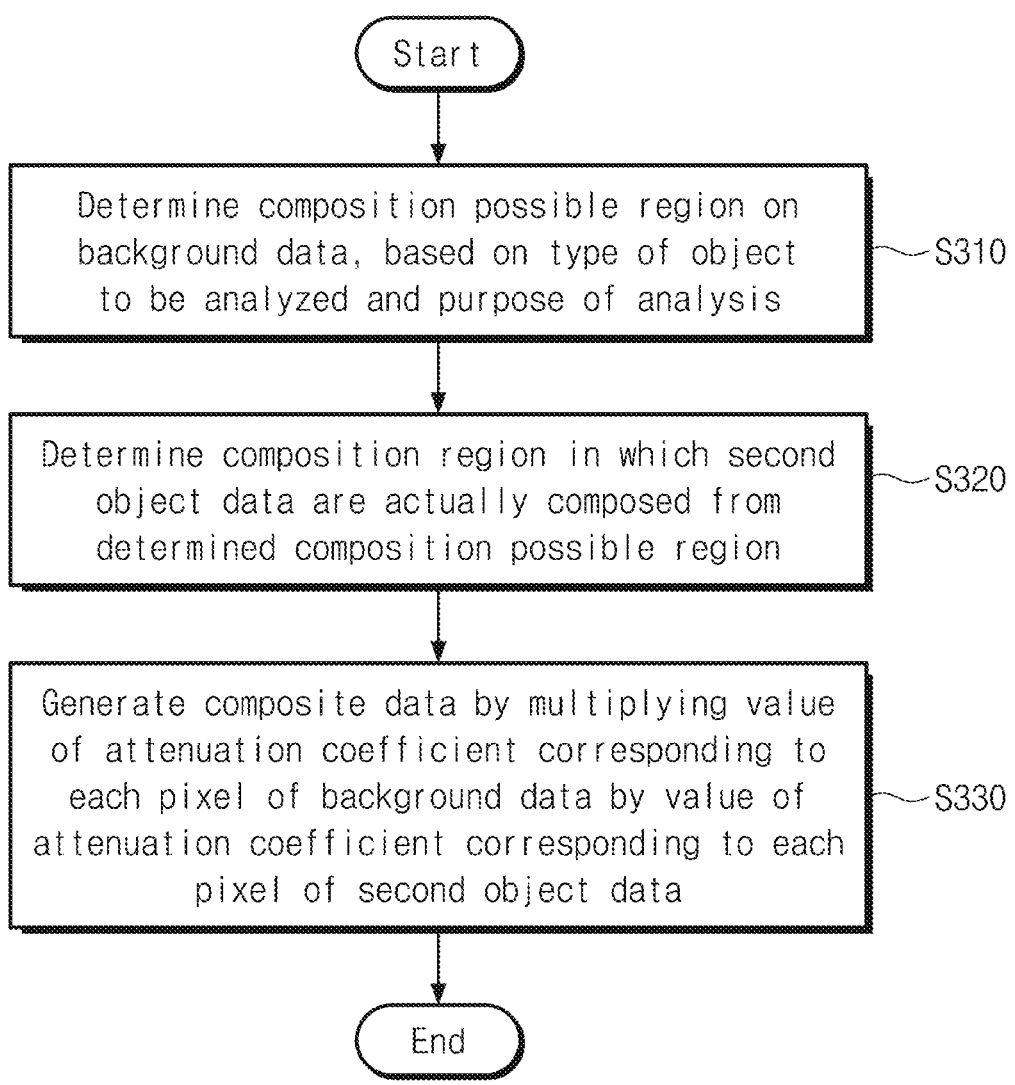
FIG. 7 is a flowchart describing a method of composing second object data with background data according to an embodiment of the inventive concept.

FIG. 7 is a flowchart describing a method of composing according to an embodiment of the inventive concept. It will be described below with reference to FIG. 1 together with FIG. 7.

In operation S310, the composition unit 113 may determine the composition possible region on the background data, based on the type of the object which are targets to be analyzed and the purpose of the analysis. In operation S320, the composition unit 113 may determine the composition region in which the second object data OBJ2 are actually composed from the determined composition possible region.

In operation S330, the composition unit 113 may generate the composite data ICOMP by multiplying the value of the attenuation coefficient corresponding to each pixel of the background data by the value of the attenuation coefficient corresponding to each pixel of the second object data OBJ2. Operation S330 is based on a feature that the intensity is attenuated when X-ray passes through the subject, and each of the plurality of pixels constituting the X-ray image represents an attenuation coefficient of the subject located in each pixel.

Figure 8:
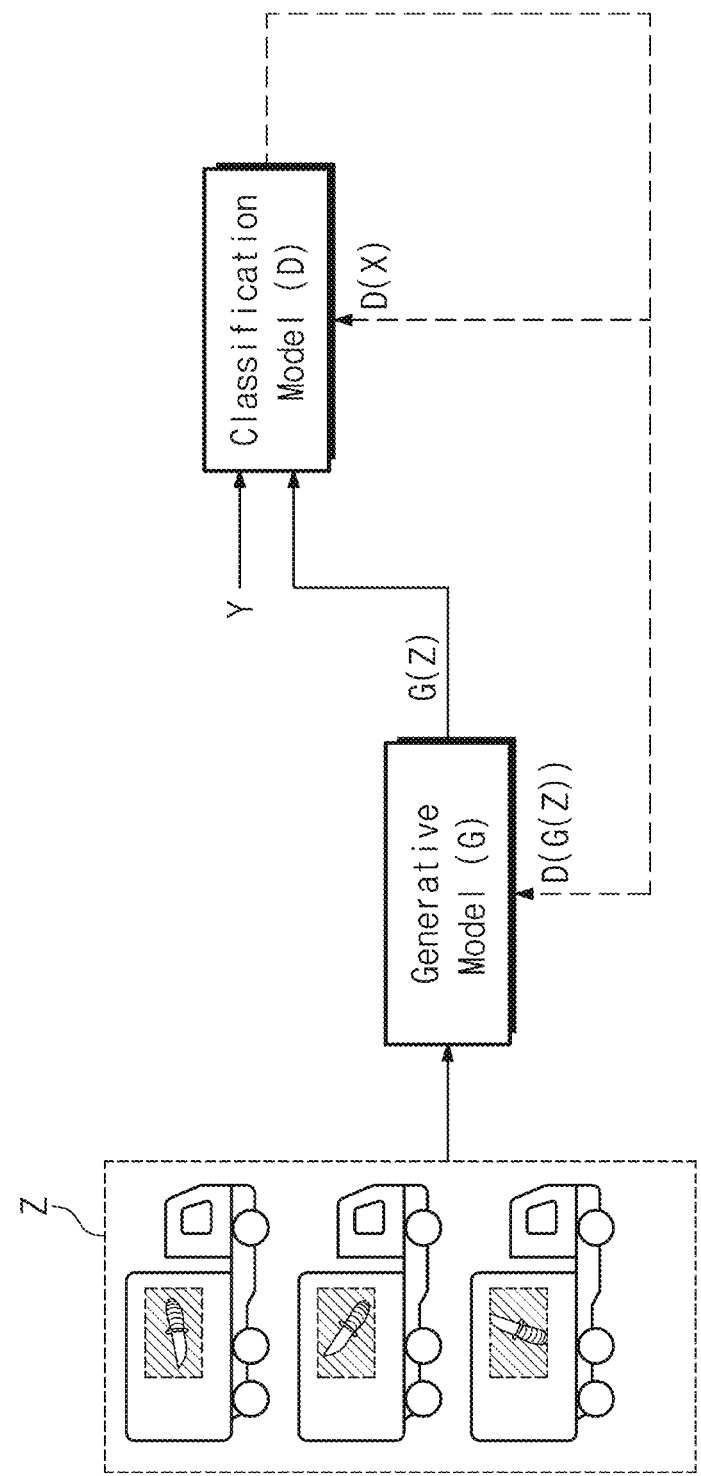
FIG. 8 is a diagram illustrating a post-processing method based on a generative adversarial network (GAN) according to an embodiment of the inventive concept.

FIG. 8 illustrates a post-processing method based on a generative adversarial network (GAN) according to an embodiment of the inventive concept. The post-processing unit 114 may include the Generative Adversarial Network (GAN). The post-processing unit 114 may generate the output data IOUT in which the sense of heterogeneity between the background data and the object is resolved based on the GAN. Hereinafter, it will be described with reference to FIG. 1 together with FIG. 8.

The GAN may include a generative model G and a classification model D. The generative model G may be implemented to receive composite data Z and to generate a plurality of composite data G(Z) in which the sense of heterogeneity is eliminated. The classification model D may receive a plurality of data G(Z) generated by the generative model G and a plurality of data Y that are not composed. In the following description, a set of the plurality of data G(Z) generated by the generative model G and the plurality of non-composite data Y is referred to as a data set X.

The classification model D may receive the data set X and may output a result D(X) of determining whether each data included in the data set X is composed. For example, when the received data are composite data, a value of D(X) may be '1', and when the received data are data that are not composed, the value of D(X) may be '0'. Accordingly, the classification model D may learn whether data are composed.

After the classification model D sufficiently learns to determine whether data are composed, the classification model D may be implemented to relearn the generative model G, based on the result of determining whether the data G(Z) generated from the generative model G are composed. Since the data (G(Z)) generated from the generative model G are composite data, a value of D(G(Z)) of a result of the composition determination determined by the classification model D may be F. In contrast, a value of D(Y) of a result of the composition determination determined by the classification model D with respect to the data Y for which the composition is not done may be '0'.

For example, when the value of D(G(Z)) of the result of the composition determination determined by the classification model D is '0', this corresponds to a case where the classification model D incorrectly determines whether the composition is done, the generative model G may be learned to additionally generate the synthetic data G(Z) in which the sense of heterogeneity is eliminated. The classification model D may relearn whether the composition is done based on the data G(Z) additionally generated from the generative model G.

By repeatedly performing the above-described process, the generative model G and the classification model D may be learned competitively with each other, and an accuracy of the determination of the classification model D on whether the composition is done with respect to the data G(Z) generated by the generative model G may be greater. When the classification model D is sufficiently learned and the accuracy of determining whether the composition is done is increased above a certain threshold, it may be determined that the generative model G is also sufficiently learned. When it is determined that the generative model G is sufficiently learned, the post-processing unit 114 may generate the composite data Z in which the sense of heterogeneity is eliminated as the output data IOUT by using only the generative model G.

Figure 9:
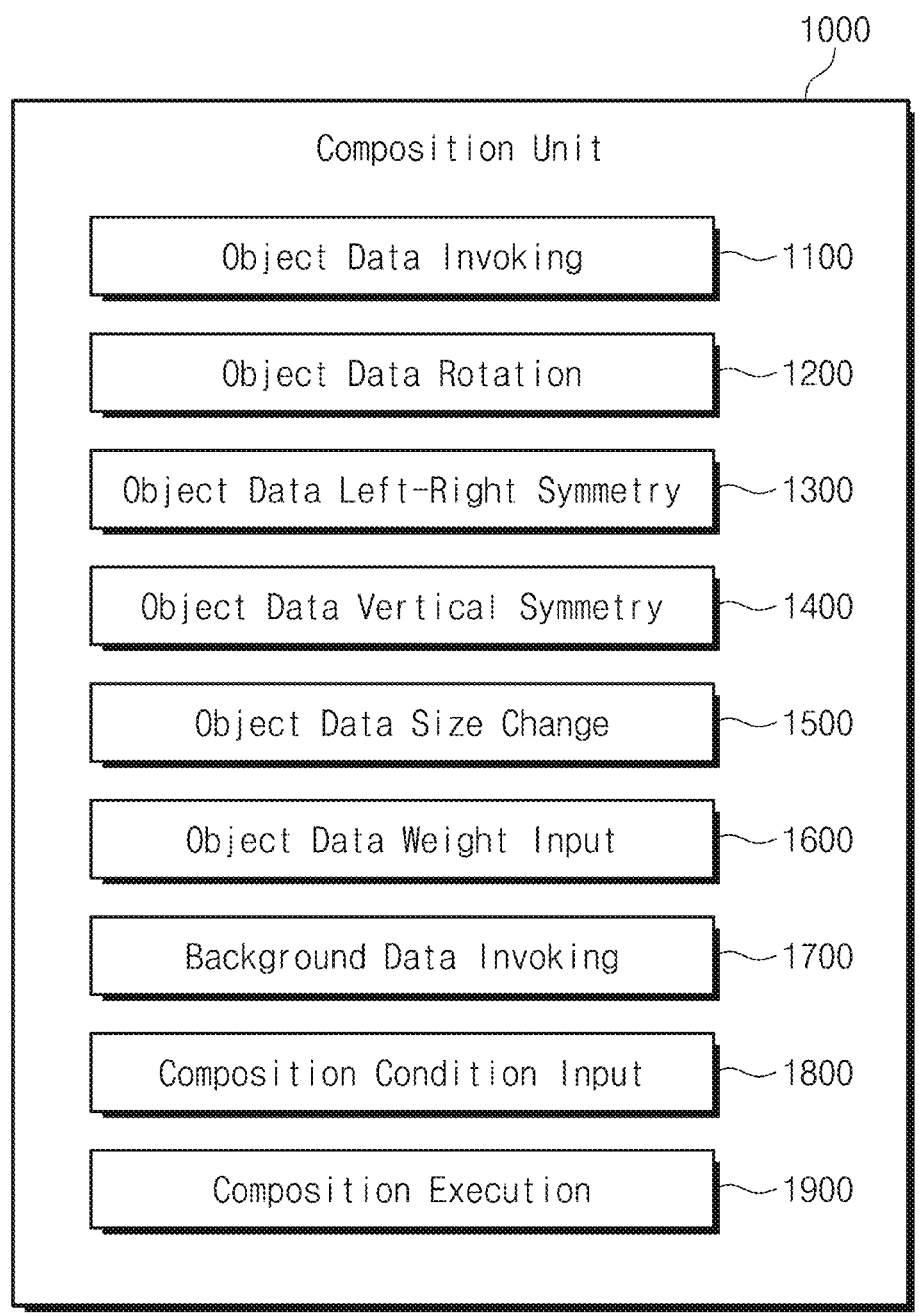
FIG. 9 is a diagram illustrating a composition unit implemented with software according to another embodiment of the inventive concept.

FIG. 9 is a diagram illustrating a composition unit 1000 implemented with software according to another embodiment of the inventive concept. The composition unit 1000 may perform the same function as the composition unit 113 of FIG. 1. The composition unit 1000 may compose the background data and the object data by multiplying the value of the attenuation coefficient corresponding to each pixel of the background data by the value of the attenuation coefficient corresponding to each pixel of the object data.

The composition unit 1000 may perform an object data invoking 1100. A user may determine whether additional data augmentation is necessary with respect to the invoked object data. When the user determines that the data augmentation is additionally necessary, the composition unit 1000 may perform an object data rotation 1200, an object data left-right symmetry 1300, an object data vertical symmetry 1400, and an object data size change 1500. Further, the composition unit 1000 may perform the object data weight input 1600 and may multiply the value of the attenuation coefficient corresponding to each pixel of the object data by the weight, such that a composed resultant object data may be seen more clearly.

The composition unit 1000 may perform a background data invoking 1700. Before performing the composition of the invoked background data and the invoked object data, the user may determine whether to directly input a composition condition (e.g., the position of the composition region). When the user directly inputs the composition condition, the composition unit 1000 may perform a composition condition input 1800. The composition unit 1000 may perform a composition execution 1900, based on the background data, the object data, and the composition condition.

Figure 10:
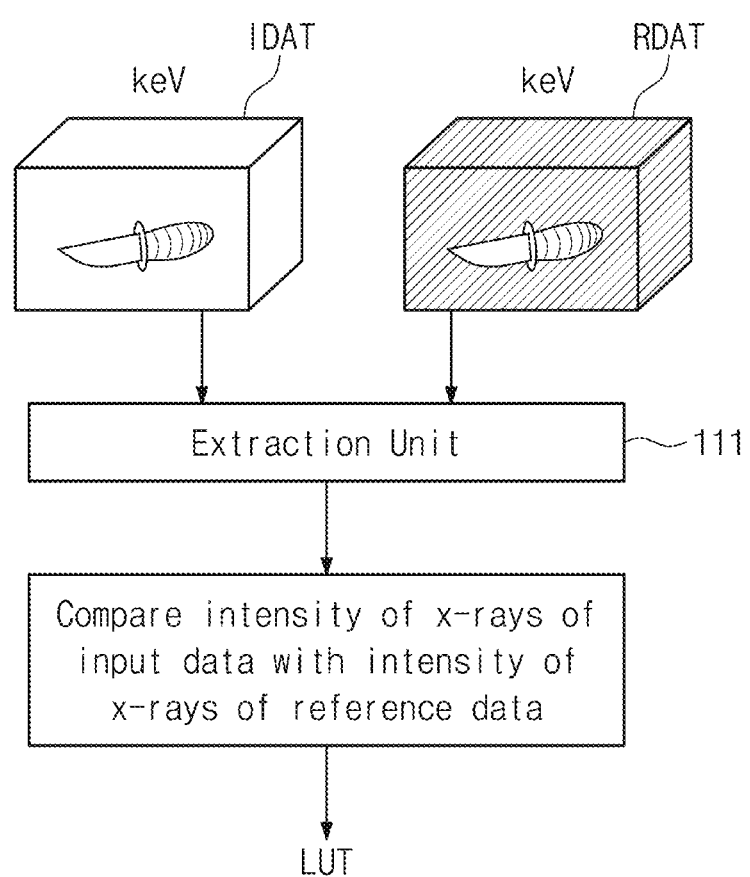
FIG. 10 is a diagram conceptually illustrating a process of generating a lookup table indicating a correspondence relationship between a photographing X-ray energy and an attenuation coefficient according to an embodiment of the inventive concept.
Figure 11:
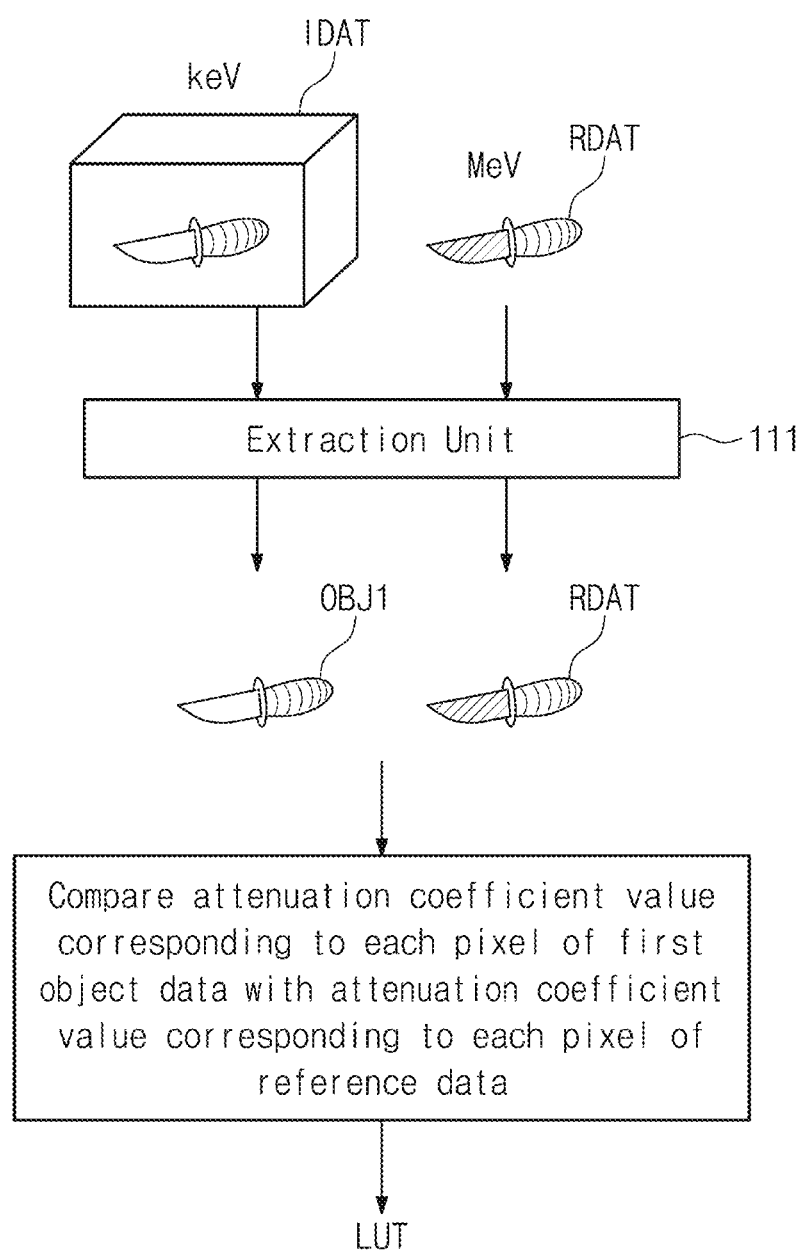
FIG. 11 is a diagram conceptually illustrating a process of generating a lookup table indicating a correspondence relationship between a photographing X-ray energy and an attenuation coefficient according to another embodiment of the inventive concept.

FIG. 10 a diagram conceptually illustrating a process of generating a lookup table LUT indicating a correspondence relationship between a photographing X-ray energy and an attenuation coefficient according to an embodiment of the inventive concept. FIG. 11 a diagram conceptually illustrating a process of generating a lookup table LUT indicating a correspondence relationship between a photographing X-ray energy and an attenuation coefficient according to another embodiment of the inventive concept. It will be described below with reference to FIG. 1 together with FIGS. 10 to 11.

Referring to FIG. 10, the extraction unit 111 may additionally receive the input data IDAT as well as 3D reference data RDAT in which the same subject as the input data IDAT is obtained by photographing at the same angle, but only the photographing energy (e.g., the X-ray energy used for the CT photographing) is set differently. Unlike the input data IDAT, the reference data RDAT indicated by hatching indicates a difference in the X-ray energy used for photographing.

For example, when the reference data RDAT is the 3D data, both the photographing X-ray energy of the input data IDAT and the photographing X-ray energy of the reference data RDAT may be in a keV band. That is, the photographing X-ray energy band of the input data IDAT may be similar to the photographing X-ray energy band of the reference data RDAT. Accordingly, it may be possible to photograph the input data IDAT and the reference data RDAT with one device.

In this case, the extraction unit 111 may generate the lookup table LUT indicating the correspondence relationship between the photographing X-ray energy and the attenuation coefficient by comparing the intensity of X-ray used for photographing the input data IDAT with the intensity of X-ray used for photographing the reference data RDAT. For example, the generated lookup table LUT may be used to convert the energy of the photographing X-ray from the keV band to the keV band. The extraction unit 111 may store the generated lookup table LUT in the buffer 120.

Referring to FIG. 11, in another embodiment, the extraction unit 111 may additionally receive the input data IDAT as well as 2D reference data RDAT (as illustrated by hatching) that are obtained by photographing a subject identical to the input data IDAT by using a 2D X-ray photographing device. The extraction unit 111 may extract the object OBJ0 which are targets to be analyzed from the input data IDAT, and may generate the first object data OBJ1 by projecting the object OBJ0 onto the 2D plane. Unlike the input data IDAT and the first object data OBJ1, the reference data RDAT represented by hatching indicates a difference in the X-ray energy used for photographing.

For example, when the reference data RDAT is the 2D data, the photographing X-ray energy of the input data IDAT may be in the keV band, and the photographing X-ray energy of the reference data RDAT may be in a MeV band. That is, the photographing X-ray energy band of the input data IDAT may be different from the photographing X-ray energy band of the reference data RDAT. Therefore, it may be impossible to photograph the input data IDAT and the reference data RDAT with one device.

In this case, the extraction unit 111 compares the attenuation coefficient value corresponding to each pixel of the first object data OBJ1 with the attenuation coefficient value corresponding to each pixel of the reference data RDAT to generate the lookup table LUT indicating the correspondence relationship between the photographing X-ray energy and the attenuation coefficient. For example, the generated lookup table LUT may be used to convert the energy of the photographing X-ray from the keV band to the MeV band. The extraction unit 111 may store the generated lookup table LUT in the buffer 120.

According to an embodiment of the inventive concept, 2D data may be acquired by extracting an object from 3D data and projecting the extracted object onto a 2D space, and X-ray data for learning may be generated by augmenting the acquired 2D data and composing the augmented 2D data with background data.

In addition, according to an embodiment of the inventive concept, high-quality X-ray data may be generated for learning a neural network for medical use and a neural network for customs detection.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the claims and their equivalents.

What is claimed is:

1. An apparatus for generating synthetic X-ray image data, the apparatus comprising:
   a processor; and
   a buffer,
   wherein the apparatus is configured to:
      receive 3D data;
      extract raw object data corresponding to a target object from the 3D data;
      project the raw object data onto a 2D plane to generate first object data;
      perform data augmentation on the first object data to generate second object data;
      compose the second object data and background data to generate composite data, the background data corresponding to a background object different from the target object and including a plurality of pixels respectively including values of corresponding X-ray attenuation coefficients; and
      perform post-processing on the composite data to generate the synthetic X-ray image data, and
   wherein the buffer stores a plurality of parameters related to generation of the first object data, the second object data, the composite data, and the synthetic X-ray image data.

2. The apparatus of claim 1, wherein extracting the raw object data comprises setting one or more virtual X-ray sources outside the raw object data, and
   wherein the first object data includes one or more images that are generated by simulating X-ray irradiation from the one or more virtual X-ray sources.

3. The apparatus of claim 1, wherein performing the data augmentation includes moving the first object data, rotating the first object data, changing a size of the first object data, or combinations thereof.

4. The apparatus of claim 1, wherein second object data includes a plurality of pixels respectively including values of corresponding X-ray attenuation coefficients, and
   wherein composing the second object data and the background data to generate the composite data comprises multiplying a value of an X-ray attenuation coefficient corresponding to a pixel of the background data by a value of an X-ray attenuation coefficient corresponding to a pixel of the second object data.

5. The apparatus of claim 4, wherein composing the second object data and the background data to generate the composite data comprises:
   generating a weight, and
   multiplying the value of the X-ray attenuation coefficient corresponding to the pixel of the second object data by the weight.

6. The apparatus of claim 1, wherein the buffer annotates the plurality of parameters with respect to the synthetic X-ray image data.

7. The apparatus of claim 1, wherein the apparatus is configured to:
   receive 3D reference data, and
   generate a lookup table that indicates a correspondence relationship between an X-ray energy corresponding to the second object data and an X-ray attenuation coefficient of the second object data by comparing an intensity of an X-ray corresponding to the 3D data with an intensity of an X-ray corresponding to the 3D reference data.

8. The apparatus of claim 7, wherein the apparatus is configured to adjust a value of the X-ray attenuation coefficient corresponding to each pixel of the second object data, based on the lookup table.

9. The apparatus of claim 1, wherein the apparatus is configured to receive 2D reference data, and
   to generate a lookup table that indicates a correspondence relationship between an X-ray energy corresponding to the second object data and an X-ray attenuation coefficient of the second object data by comparing a value of the X-ray attenuation coefficient corresponding to each pixel of the first object data with a value of the X-ray attenuation coefficient corresponding to each pixel of the 2D reference data.

10. The apparatus of claim 9, wherein the apparatus is configured to adjust the value of the X-ray attenuation coefficient corresponding to each pixel of the second object data, based on the lookup table.

11. A method for generating synthetic X-ray image data, the method comprising:
    extracting raw object data corresponding to a target object from 3D data;
    generating first object data by projecting the raw object data onto a 2D plane;
    generating second object data by performing data augmentation on the first object data;
    generating composite data by composing the second object data with background data, the background data corresponding to a background object different from the target object and including a plurality of pixels respectively including values of corresponding X-ray attenuation coefficients; and
    generating the synthetic X-ray image data by performing post-processing on the composite data.

12. The method of claim 11, wherein generating the first object data includes:
    setting one or more virtual X-ray sources; and
    generating one or more images by simulating X-ray irradiation from the one or more virtual X-ray sources.

13. The method of claim 11, wherein generating the second object data includes:
    performing a data move with respect to the first object data;
    performing a data rotation with respect to the first object data;
    performing a data size conversion with respect to the first object data; or combinations thereof.

14. The method of claim 11,
    wherein the background data includes a plurality of pixels values of corresponding X-ray attenuation coefficients,
    wherein the second object data includes a plurality of pixels respectively including values of corresponding X-ray attenuation coefficients, and
    wherein generating the composite data includes:
    multiplying a value of an X-ray attenuation coefficient corresponding to a pixel of the background data by a value of an X-ray attenuation coefficient corresponding to a pixel of the second object data.

15. The method of claim 14, wherein generating the composite data further includes:
   generating a weight; and
   multiplying the value of the X-ray attenuation coefficient corresponding to each pixel of the second object data by the weight.

16. A non-transitory computer-readable medium storing program code that, when is executed by a processor, causes the processor to:
   extract raw object data corresponding to a target object from 3D data;
   generate first object data by projecting the raw object data onto a 2D plane;
   generate second object data by performing data augmentation on the first object data;
   generate composite data by composing the second object data with background data; and
   generate output data by performing post-processing on the composite data,
   wherein the background data corresponds to a background object different from the target object and includes a plurality of pixels respectively including values of corresponding X-ray attenuation coefficients.

* * * * *